(12) United States Patent
Walden et al.

(10) Patent No.: US 8,247,499 B2
(45) Date of Patent: Aug. 21, 2012

(54) WATER-ABSORBING POLYMER STRUCTURE WITH IMPROVED ABSORPTION PROPERTIES

(75) Inventors: Mirko Walden, Herten (DE); Franck Furno, Düsseldorf (DE); Harald Schmidt, Tonisvorst (DE)

(73) Assignee: Evonik Stockhausen GmbH, Krefeld (DE)

( * ) Notice: Subject to any disclaimer, the term of this patent is extended or adjusted under 35 U.S.C. 154(b) by 735 days.

(21) Appl. No.: 11/912,219

(22) PCT Filed: Apr. 21, 2006

(86) PCT No.: PCT/EP2006/003696
§ 371 (c)(1),
(2), (4) Date: Jan. 16, 2009

(87) PCT Pub. No.: WO2006/111404
PCT Pub. Date: Oct. 26, 2006

(65) Prior Publication Data
US 2008/0221277 A1 Sep. 11, 2008

(30) Foreign Application Priority Data

Apr. 22, 2005 (DE) .......................... 10 2005 018 923
Dec. 27, 2005 (DE) .......................... 10 2005 062 831

(51) Int. Cl.
*C08F 8/42* (2006.01)
*C08J 3/24* (2006.01)

(52) U.S. Cl. ............... 525/330.2; 525/329.7; 525/329.5; 525/330.6; 525/361; 525/362; 525/363; 525/370; 525/371; 525/372; 525/373; 524/413; 524/431; 524/556; 524/560

(58) Field of Classification Search ............... 525/329.7, 525/329.5, 330.2, 330.6, 361, 362, 363, 370, 525/371, 372, 373; 524/413, 431, 556, 560
See application file for complete search history.

(56) References Cited

U.S. PATENT DOCUMENTS

| | | | |
|---|---|---|---|
| 4,076,663 A | 2/1978 | Masuda et al. | |
| 4,131,576 A | 12/1978 | Iovine et al. | |
| 4,179,367 A | 12/1979 | Barthell et al. | |
| 4,286,082 A | 8/1981 | Tsubakimoto et al. | |
| 4,340,706 A | 7/1982 | Obayashi et al. | |
| 4,587,308 A | 5/1986 | Makita et al. | |
| 5,409,771 A | 4/1995 | Dahmen et al. | |
| 5,587,308 A | 12/1996 | Carter et al. | |
| 5,610,220 A | 3/1997 | Klimmek et al. | |
| 5,672,633 A | 9/1997 | Brehm et al. | |
| 5,712,316 A | 1/1998 | Dahmen et al. | |
| 5,973,042 A * | 10/1999 | Yoshinaga et al. ............ 524/192 |
| 6,060,557 A | 5/2000 | Dahmen et al. | |
| 6,403,700 B1 | 6/2002 | Dahmen et al. | |
| 6,605,673 B1 | 8/2003 | Mertens et al. | |
| 6,620,889 B1 | 9/2003 | Mertens et al. | |
| 7,179,862 B2 | 2/2007 | Mertens et al. | |
| 2003/0040570 A1 | 2/2003 | Nestler et al. | |
| 2003/0125684 A1 | 7/2003 | Qin | |
| 2006/0029782 A1 | 2/2006 | Harren et al. | |
| 2006/0057389 A1 | 3/2006 | Reimann et al. | |
| 2007/0066754 A1 | 3/2007 | Loeker et al. | |
| 2007/0101644 A1 * | 5/2007 | Fujimaru et al. ......... 47/58.1 SC |
| 2007/0129495 A1 | 6/2007 | Mertens et al. | |

FOREIGN PATENT DOCUMENTS

| | | |
|---|---|---|
| DE | 2612846 | 10/1976 |
| DE | 2706135 | 8/1978 |
| DE | 2840010 | 6/1979 |
| DE | 3503458 | 8/1985 |
| DE | 3713601 | 11/1988 |
| DE | 4020780 C1 | 8/1991 |
| DE | 4244548 | 7/1994 |
| DE | 4418818 | 1/1995 |
| DE | 4333056 | 3/1995 |
| DE | 19529348 A1 | 2/1997 |
| DE | 19909653 A1 | 9/2000 |
| DE | 19909838 A1 | 9/2000 |
| DE | 10138630 A1 | 2/2003 |
| DE | 10334286 | 3/2005 |
| WO | 9605234 A1 | 2/1996 |
| WO | 9934843 A1 | 7/1999 |
| WO | 02056812 | 7/2002 |
| WO | 2004037900 | 5/2004 |
| WO | 2004037903 A2 | 5/2004 |
| WO | WO 2005/053381 A1 * | 6/2005 |

OTHER PUBLICATIONS

English Translation of International Preliminary Report on Patentability mailed on Apr. 24, 2008 in PCT/EP2006/003696.
International Preliminary Report on Patentability mailed on Aug. 1, 2007 in PCT/EP2006/003696.

* cited by examiner

*Primary Examiner* — Roberto Rabago
(74) *Attorney, Agent, or Firm* — Smith Moore Leatherwood LLP; Philip P. McCann

(57) ABSTRACT

A water-absorbing polymer structure is disclosed, whose surface has been brought into contact with a combination of a metal salt and an oxide of a metal. The invention also relates to a process for treating the surface of water-absorbing polymer structures whereby the surface of water-absorbing polymer structures is brought into contact with a combination of a metal salt and an oxide of a metal at a temperature of from about 50 to about 300° C. The present invention further relates to the water-absorbing polymer structures obtainable by this process, a composite comprising a water-absorbing polymer structure and a substrate, chemical products such as foams and fibers comprising water-absorbing polymer structures or a composite, and the use of a combination of an oxide of a metal and of a metal salt for treatment of the surface of super-absorbing polymer structures.

10 Claims, No Drawings

WATER-ABSORBING POLYMER STRUCTURE WITH IMPROVED ABSORPTION PROPERTIES

This application is a national stage application under 35 U.S.C. 371 of international application No. PCT/EP2006/003696 filed 21 Apr. 2006, and claims priority to German Application Nos. DE 10 2005 018 923.7-44 and DE 10 2005 062 831.1 filed 22 Apr. 2005 and 27 Dec. 2005, respectively, the disclosures of which are expressly incorporated herein by reference.

BACKGROUND

The present invention relates to water-absorbing polymer structures, a process for treatment of the surface of water-absorbing polymer structures, the surface-treated, water-absorbing polymer structures obtainable by this process, a composite comprising a water-absorbing polymer structure and a substrate, a process for production of a composite, the composite obtainable by this process, chemical products such as foams, formed bodies, and fibers comprising water-absorbing polymer structures or a composite, the use of water-absorbing polymer structures or of a composite in chemical products as well as the use of a combination of an oxide of a metal and of a metal salt for treatment of the surface of superabsorbing polymer structures.

Superabsorbers are water-insoluble, crosslinked polymers, which are capable of absorbing, and retaining under a given pressure, large quantities of aqueous liquids, in particular body fluids, such as urine or blood, by swelling and forming hydrogels. Because of these characteristic properties, these polymers principally find applications by incorporation into sanitary articles, such as, for example, baby diapers, incontinence products, or sanitary napkins.

The production of the superabsorbers generally occurs by radical polymerization of acid groups-carrying monomers in the presence of crosslinkers. In this way, by the choice of the monomer composition, the crosslinkers and the polymerization conditions and the processing conditions for the hydrogel obtained after the polymerization, polymers with different absorption properties can be prepared. Further possibilities are offered by the production of graft polymers, for example by using chemically modified starches, celluloses, and polyvinyl alcohol according to DE-OS 26 12 846.

DE 40 20 780 C1 discloses the post-treatment of superabsorbing polymers by post-crosslinking of the surfaces of the polymer particles. By means of the post-crosslinking of the surface of the water-absorbing polymer particles, in particular the absorption capacity of the polymer particles under the action of pressures is increased.

DE 199 09 653 A1 and DE 199 09 838 A1 describe powdery, surface post-crosslinked polymers which absorb water-aqueous or serous liquids or blood, which are based on acid groups-carrying monomers and which has been coated with a surface post-crosslinking agent and a cation in aqueous solution and post-crosslinked. The polymers disclosed in this state of the art have advantageous absorption properties compared to previous polymers, in particular a high permeability.

The surface post-crosslinking of the polymer structures disclosed in the above-cited state of the art leads to an increase of the absorption capacity under a pressure; however, a reduction of the retention capacity is generally linked with this surface post-crosslinking. Conversely, an increase of the retention capacity effected, for example, by a low degree of primary crosslinking, leads to reduced absorption capacity of the polymer structure under pressure. A reduced retention capacity of the polymer structure has, however, the disadvantage that hygiene articles, such as, for example, diapers, which comprise these polymer structures, are characterized by a decreased absorption and retention capacity of body fluids, while a reduced absorption under pressure in particular leads to the hygiene articles not being able to absorb liquids sufficiently while under a pressure, such as a pressure caused, for example, by a sitting diaper wearer.

Polymer structures which unite a good retention behavior and a good absorption capacity under a pressure could possibly be obtained by subjecting an originally only lightly crosslinked polymer particle, which, because of the low degree of crosslinking, has a comparatively high retention, to a surface post-crosslinking. This has, however, the disadvantage, that the superabsorbers obtained in this way are characterized by a high content in soluble parts, since the content in soluble parts increases with a decreasing degree of crosslinking. An increasing content in soluble parts is, however, linked with a decreased skin tolerance, so that hygiene articles comprising polymer structures with a high content of soluble parts are of concern from a dermatological viewpoint. In order to maintain the content in the soluble parts in the polymer structures as low as possible, a minimum amount of primary crosslinking in the polymer structure is desirable.

The present invention had the object of overcoming the disadvantages arising from the state of the art.

In particular, the present invention has the object of providing superabsorbers that are characterized by, in addition to excellent retention properties, also by good absorption properties under a pressure, as well as advantageously also by a good skin tolerance.

Furthermore, the present invention has the object of providing a process with which advantageous superabsorbers of this type, as well as a composite comprising these superabsorbers, can be prepared. In particular, it should be possible by this process to improve the retention and the absorption capacity of the superabsorber under a pressure independently from each other.

The present invention also had the object of providing hygiene articles with a high content in water-absorbing polymer structures, which are characterized by a particularly good skin tolerance and furthermore good absorption properties, in particular a good absorption capacity for body fluids.

SUMMARY

A contribution to the solution of the above-mentioned objects is provided by a water-absorbing polymer structure, whose surface has been brought into contact with a combination of a metal salt and an oxide of a metal.

It has been found that the retention properties of superabsorber particles may be improved, for example, by the treatment of the surfaces of water-absorbing polymer structures with a combination of a metal salt and an oxide of a metal. In particular, it was observed that by the surface treatment of the water-absorbing polymer structures with the combination of a metal salt and the oxide of a metal, the reduction of the retention observed with the surface post-crosslinking may be considerably less than for surface post-crosslinked polymer structures, whose surface has not been brought into contact with this combination of a metal salt and an oxide of a metal. By means of the surface modification according to the invention, it is, for example, possible to improve, by means of a surface treatment occurring after the polymerization, the retention capacity of polymer structures with a high degree of primary crosslinking, which are characterized by a correspondingly low content in soluble parts and a correspondingly low retention capacity, so that polymer structures with an excellent R/LA ratio can be obtained.

Preferred polymer structures according to the invention are fibers, foams, or particles.

Polymer fibers may be dimensioned so that they can be incorporated in or as yarns for textiles and also directly in textiles. The polymer fibers may have a length from about 1 to about 500 mm, or from about 2 to about 500 mm, or from about 5 to about 100 mm, and have a diameter from about 1 to about 200 Denier, or from about 3 to about 100 Denier, or from about 5 to about 60 Denier.

Polymer particles may be dimensioned so that they have an average particle size according to ERT 420.2-02 from about 10 to about 3,000 µm, or from about 20 to about 2,000 µm, or from about 150 to about 850 µm, or from about 150 to about 600 µm. A portion of polymer particles may have a particle size from about 300 to about 600 µm of at least about 30 wt %, or at least about 40 wt %, or at least about 50 wt %, based upon the total weight of the post-crosslinked, water-absorbing polymer particles.

In an embodiment of the water-absorbing polymer structures according to the invention, the water-absorbing polymer structures may be based upon ($\alpha$1) from about 20 to about 99.999 wt %, or from about 55 to about 98.99 wt %, or from about 70 to about 98.79 wt % of polymerized, ethylenically unsaturated, acid groups-carrying monomers or salts thereof, or polymerized, ethylenically unsaturated monomers comprising a protonated or quaternated nitrogen, or mixtures thereof, whereby mixtures comprising at least ethylenically unsaturated, acid groups-comprising monomers, preferably acrylic acid, are particularly preferred, ($\alpha$2) from 0 to about 80 wt %, or from 0 to about 44.99 wt %, from 0.1 to about 44.89 wt % of polymerized, monoethylenically unsaturated monomers which are co-polymerizable with ($\alpha$1), ($\alpha$3) from 0.001 to about 5 wt %, or from 0.01 to about 3 wt %, or from 0.01 to about 2.5 wt % of one or more crosslinkers, ($\alpha$4) from 0.001 to about 5 wt %, or from 0.01 to about 2.5 wt %, or from 0.1 to about 1 wt % of the metal salt, ($\alpha$5) from 0.001 to about 5 wt %, or from 0.01 to about 2.5 wt %, or from 0.1 to about 1 wt % of the oxide of the metal, ($\alpha$6) from 0 to about 30 wt %, or from 0 to about 5 wt %, or from 0.1 to about 5 wt % of a water-soluble polymer, ($\alpha$7) from 0 to about 20 wt %, or from about 2.5 to about 15 wt %, or from about 5 to about 10 wt % water, and ($\alpha$8) from 0 to about 20 wt %, or from 0 to about 10 wt %, or from 0.1 to about 8 wt % of one or more additives, whereby the sum of the weight amounts ($\alpha$1) to ($\alpha$8) is 100 wt %.

The monoethylenically unsaturated, acid groups-comprising monomers ($\alpha$1) may be partially or fully neutralized. The monoethylenically unsaturated, acid groups-comprising monomers may be neutralized to at least about 25 mol %, or to at least about 50 mol %, or from about 50 to about 80 mol %. In this context, reference is made to DE 195 29 348 A1. The neutralization may also occur partially or fully after the polymerization. Furthermore, the neutralization may be carried out with alkali metal hydroxides, alkaline earth metal hydroxides, ammonia, carbonates, and bicarbonates. In addition, any further base that forms a water-soluble salt with the acid is conceivable. A mixed neutralization with different bases is also conceivable. Neutralization with ammonia and alkali metal hydroxides, sodium hydroxide, or with ammonia are examples.

The free acid groups may predominate in a polymer, so that this polymer has a pH value lying in the acidic region. This acidic water-absorbing polymer may be at least partially neutralized by a polymer with free basic groups, preferably amine groups, which is basic compared to the acidic polymer. These polymers are described in the literature as "Mixed-Bed Ion-Exchange Absorbent Polymers" (MBIEA-Polymers) and are disclosed in WO 99/34843 A1, among others. As a rule, MBIEA polymers have a composition that comprises on the one hand basic polymers, which are able to exchange anions, and on the other hand, a polymer which is acidic in comparison to the basic polymer, which is capable of exchanging cations. The basic polymer comprises basic groups and is typically obtained by polymerization of monomers which carry basic groups, or groups which can be converted into basic groups. These monomers may comprise primary, secondary, or tertiary amines or corresponding phosphines or at least two of the above functional groups. In particular ethyleneamine, allylamine, diallylamine, 4-aminobutene, alkyloxycycline, vinylformamide, 5-aminopentene, carbodiimide, formaldacine, melamine, and the like, as well as their secondary or tertiary amine derivatives, belong to this group of monomers.

Ethylenically unsaturated, acid groups-comprising monomers ($\alpha$1) may include those compounds that are mentioned as ethylenically unsaturated acid groups-comprising monomers ($\alpha$1) in WO 2004/037903 A2, which is hereby incorporated as reference only as to the listing of ethylenically unsaturated, acid groups-comprising monomers ($\alpha$1) and thus forms part of the disclosure. Examples of ethylenically unsaturated, acid groups-comprising monomers ($\alpha$1) are acrylic acid and methacrylic acid.

According to an embodiment of the process according to the invention, water-absorbing polymer structures may be used, in which the monoethylenically unsaturated monomers ($\alpha$2) that are co-polymerizable with ($\alpha$1) may be selected from acrylamides, methacrylamides, or vinylamides.

Examples of (meth)acrylamides include, besides acrylamide and methacrylamide, alkyl-substituted (meth)acrylamides or aminoalkyl-substituted derivatives of (meth)acrylamide, such as N-methylol(meth)acrylamide, N,N-dimethylamino(meth)acrylamide, dimethyl(meth)acrylamide, or diethyl(meth)acrylamide. Possible vinyl amides are, for example, N-vinylamides, N-vinylformamides, N-vinylacetamides, N-vinyl-N-methylacetamide, N-vinyl-N-methylformamides, and vinylpyrrolidone.

According to another embodiment of the process according to the invention, water-absorbing polymer structures may be used, in which the monoethylenically unsaturated monomers ($\alpha$2) that are co-polymerizable with ($\alpha$1) are water-soluble monomers. In this context, alkoxypolyalkalineoxide (meth)acrylates such as methoxypolyethylene glycol (meth)acrylates are examples.

Monoethylenically unsaturated monomers ($\alpha$2) that are co-polymerizable with ($\alpha$1) may be water-dispersible monomers such as acrylic acid esters and methacrylic acid esters, such as methyl(meth)acrylate, ethyl(meth)acrylate, propyl(meth)acrylate, or butyl (meth)acrylate.

The monoethylenically unsaturated monomers ($\alpha$2) that are co-polymerizable with ($\alpha$1) may further comprise methylpolyethylene glycol allylethers, vinylacetate, styrene, and isobutylene.

Crosslinker ($\alpha$3) may include compounds that are mentioned in WO 2004/037903 A2 as crosslinker ($\alpha$3). Among these are crosslinkers, water-soluble crosslinkers, including N,N'-methylenebisacrylamide, polyethylene glycol di(meth)acrylates, triallylmethylammonium chloride, tetraallylammonium chloride, as well as allylnonaethylene glycol acrylate prepared with 9 mol ethylene oxide per mol of acrylic acid.

As metal salt ($\alpha 4$), all metal salts known to the skilled person may be used, whereby water-soluble metal salts are examples. By "water-soluble" is understood to mean metal salts, of which at a temperature of 25° C., at least 1 g, or at least 10 g, or at least 100 g, or at least 500 g are soluble in 1 liter of distilled water.

The water-soluble metal salts may include particular sulfates, sulfites, sulfides, chlorides, bromides, iodides, nitrates, nitrites, phosphates, phosphites, carbonates, hydrogen carbonates, hydroxides, acetates, lactates, and oxalates.

The metal cation of the metal salt may be a monovalent, divalent, or a trivalent metal cation. Examples of metal cations are $Na^+$, $K^+$, $Li^+$, $Mg^{2+}$, $Ca^{2+}$, $Fe^{2+}$, $Fe^{3+}$, $Ag^+$, $Cu^+$, $Cu^{2+}$, $Zn^{2+}$ and $Al^{3+}$. The following metal salts may be used as surface treatment agent in the water-absorbing polymer structures according to the invention: aluminum chloride, polyaluminum chloride, aluminum sulfate, aluminum nitrate, bis-aluminum potassium sulphate, bis-aluminum sodium sulfate, aluminum lactate, aluminum oxalate, aluminum citrate, aluminum glyoxylate, aluminum succinate, aluminum itaconate, aluminum crotonate, aluminum butyrate, aluminum sorbate, aluminum malonate, aluminum benzoate, aluminum tartrate, aluminum pyruvate, aluminum valerate, aluminum formate, aluminum glutarate, aluminum propanate, or aluminum acetate, whereby $AlCl_3 \times 6H_2O$, $NaAl(SO_4)_2 \times 12H_2O$, $Al(NO_3)_3 \times 9H_2O$, $KAl(SO_4)_2 \times 12H_2O$, or $Al_2(SO_4)_3 \times 14\text{-}18H_2O$ as well as the corresponding anhydrous salts, $Na_2SO_4$ or hydrates thereof, $MgSO_4 \times 10H_2O$, or anhydrous magnesium sulphate are specific examples.

As oxide of a metal, pulverulent oxides may be used wherein at least about 50 wt %, or at least about 75 wt %, or at least about 90 wt. % of the oxide of the metal have a particle size determined by sieve analysis (for particle sizes greater than 10 μm) or laser diffractometry (for particle sizes smaller than 10 μm) from about 10 to about 1,000,000 nm, or from about 12 to about 500,000 nm, or from about 15 to about 5,000 nm. The oxide of the metal may have a weight average of the particle size within a range from about 15 to about 5000 nm, or from about 20 to about 3000 nm, or from about 100 to about 2,000 nm.

As oxide of a metal, all metal oxides may be used, whereby as "oxide of a metal", the oxides of semi-metals, such as boron, silicon, or germanium are not comprised.

The water-absorbing polymer structures according to the invention may comprise as oxide of a metal, an oxide of a transition metal, whereby among the transition metals zinc is an example.

In a particular embodiment of the water-absorbing polymer structures according to the invention, these may comprise, as oxide of a metal, a fine particulate zinc oxide, which is based to at least about 50 wt % upon optionally agglomerated particles with a particle size from about 10 nm to about 500 μm. Such fine particulate zinc oxides may, for example, be obtainable under the trade name "Nanox®" from Elementis Specialities, USA.

Water-absorbing polymer structures according to the invention may be polymer structures, whose surface have been brought into contact with a water-soluble salt of aluminum as metal salt, and with a pulverulent zinc oxide as oxide of a metal.

Water-soluble polymers ($\alpha 6$) may include water-soluble polymers, such as partially or fully saponified polyvinyl alcohol, polyvinyl pyrrolidone, starches, or starch derivatives, polyglycols, or polyacrylic acids may be polymerized into the polymer structures. The molecular weight of these polymers may not be critical, as long as they are water-soluble. Water-soluble polymers may include starches, starch derivatives, or polyvinyl alcohol. The water-soluble polymers, may be synthetic such as polyvinyl alcohol, may also serve as graft basis for the monomers to be polymerized.

Additive ($\alpha 8$) may include suspending agents, odor binders, surfactants, or anti-oxidants, as well as those additives which were used in the production of the polymer structures (initiators, etc.).

The polymer structures may have at least about 50 wt %, or at least about 70 wt %, or at least about 90 wt % on carboxylate groups-carrying monomers. Furthermore, the component ($\alpha 1$) may consist to at least about 50 wt %, or to at least about 70 wt % of acrylic acid, which may be neutralized to at least about 20 mol %, or to at least about 50 mol %, or from about 60 to about 85 mol %.

The polymer structures according to the invention may have a core-shell structure and comprise an inner region (core) and an outer region (shell) surrounding the inner region, whereby the polymer structure is more strongly crosslinked in the outer region than in the inner region.

The water-absorbing polymer structures according to the invention, whose surfaces have been brought into contact with a metal salt and an oxide of a metal may be characterized by an R/LA ratio of at least about 2.00 g/g %, or of at least about 2.59 g/g %, or of at least about 2.8 g/g %, or at least about 3 g/g %. R is the CRC value (CRC=Centrifugation Retention Capacity; in the case of particles, respectively determined for the total particle fraction) determined according to ERT 441.2-02 (ERT=Edana Recommended Test Method), and LA is the content in extractables (soluble parts) determined according to ERT 470.2-02.

Furthermore, the water-absorbing polymer structures according to the invention may be characterized by an absorption under a pressure of 50 g/cm$^2$ determined according to ERT 442.2-02 of at least about 15 g/g, or at least about 17 g/g, or at least about 19 g/g (in the case of particles, respectively determined for the total particle fraction).

A contribution to the solution of the above-mentioned objects may also be provided by a process for treatment of the surface of water-absorbing polymer structures, comprising the following steps:

i) providing an untreated, water-absorbing polymer structure; and ii) bringing into contact of the surface of the untreated, water-absorbing polymer structure with a combination of a metal salt and an oxide of a metal at a temperature of from about 100 to about 300° C., or from about 125 to about 250° C., or from about 150 to about 200° C.

"Untreated" in the context of the present invention means that the water-absorbing polymer structure has not yet been brought into contact with the combination of a metal salt and an oxide of a metal. The term "untreated" does not, however, exclude that the water-absorbing polymer structures may be modified by means of other surface modification measures, such as, for example, surface post-crosslinking. The untreated water-absorbing polymer structure may have a CRC value determined according to ERT 441.2-02 of at least about 30 g/g, or at least about 35 g/g, or at least about 36 g/g, or at least about 38 g/g, or at least about 40 g/g, whereby a CRC value of about 75 g/g, or about 70 g/g, or about 65 g/g, or about 60 g/g, or about 55 g/g is not exceeded (in the case of particles, respectively determined for the total particle fraction). Furthermore, the term "untreated water-absorbing polymer structure" may also comprise polymer structures that are not yet completely dry and still have a water content of more than about 10 wt %, or more than about 20 wt %, or more than about 30 wt %, whereby the water content should not exceed about 75 wt %, or does not exceed about 50 wt %, respectively based on the total weight of the untreated, water-polymer structure.

As untreated, water-absorbing polymer structures, polymers may be used in the process according to the invention, which may have been obtained by a process comprising the following steps:
a) radical polymerization of acid groups-carrying, ethylenically unsaturated, optionally partially neutralized monomers in the presence of a crosslinker to form a hydrogel;
b) optionally, commination of the hydrogel;
c) drying of the optionally comminuted hydrogel to obtain water-absorbing polymer structures;
d) optionally, milling of the thus-obtained absorbing polymer structures and sieving to a desired particle size fraction;
e) optionally, further surface modifications of the thus-obtained water-absorbing polymer structures.

The "untreated" polymer structure obtained in this way may then be brought into contact with the combination of a metal salt and a metal oxide, whereby the metal salt and the oxide of the metal in the form of a fluid $F_1$ comprising a solvent, the metal salt and the oxide of the metal, may be brought into contact with the water-absorbing polymer structure. As solvent, such as water or organic solvents that are miscible with water such as, for example, methanol, ethanol, 1-propanol, 2-propanol, or 1-butanol, or mixtures of at least two of these solvents are used. The metal salt may be comprised in the fluid $F_1$ in an amount of from about 0.1 to about 50 wt %, or from about 1 to about 40 wt %, or from about 5 to about 25 wt %, and the oxide of the metal is comprised in the fluid $F_1$ in an amount of from about 0.1 to about 50 wt %, or from about 1 to about 40 wt %, or from about 5 to about 25 wt %, respectively based upon the total weight of the solvent. It is also conceivable to use the metal salt and the oxide of the metal in separate fluids.

The metal salt may be brought into contact with the untreated water-absorbing polymer structure, in an amount of from 0.001 to about 5 wt %, or from 0.01 to about 2.5 wt %, or from 0.1 to about 1 wt %, and the oxide of the metal in an amount of from 0.001 to about 5 wt %, or from 0.01 to about 2.5 wt %, or from 0.1 to about 1 wt %, respectively based on the weight of the untreated water-absorbing polymer structure.

As metal salt and oxide of a metal salt may include those compounds that have been mentioned above in connection with the water-absorbing polymer structures according to the invention as preferred components ($\alpha4$) and ($\alpha5$).

Suitable mix aggregates for applying the fluid $F_1$ may be Patterson-Kelley mixer, DRAIS turbulence mixer, Lodige mixer, Ruberg mixer, screw mixer, plate mixer, and fluidized bed mixer as well as continuously operating vertical mixers in which the polymer structure is mixed at high frequency by means of rotating knives (Schugi mixer).

The radical polymerization occurring in process step a) preferably occurs in aqueous solution, whereby this aqueous solution preferably comprises, in addition to water as solvent
($\alpha1$) the ethylenically unsaturated, acid groups-carrying monomers or salts thereof, whereby acrylic acid is particularly preferred as acid groups-carrying monomer,
($\alpha2$) optionally, monoethylenically unsaturated monomers which are co-polymerizable with ($\alpha1$),
($\alpha3$) the crosslinker,
($\alpha6$) optionally, a water-soluble polymer, as well as
($\alpha8$) optionally, one or more additives.

As ethylenically unsaturated, acid groups-carrying monomers ($\alpha1$), as monoethylenically unsaturated monomers ($\alpha2$) which are co-polymerizable with ($\alpha1$), as crosslinker ($\alpha3$), as water-soluble polymers ($\alpha6$) and as additive ($\alpha8$), may include those compounds that have already been mentioned in connection with the polymer structures according to the invention as ethylenically unsaturated acid groups-carrying monomers ($\alpha1$), as monoethylenically unsaturated monomers ($\alpha2$) which are co-polymerizable with ($\alpha1$), as crosslinker ($\alpha3$), as water-soluble polymers ($\alpha6$), and as additive ($\alpha8$).

Water-absorbing polymer structures may be prepared from the above-mentioned monomers, co-monomers, crosslinkers, water-soluble polymers, and additives by various polymerization methods. Bulk polymerization, which may occur in kneader reactors such as extruders, solution polymerization, spray polymerization, inverse emulsion polymerization, and inverse suspension polymerization can, for example, be mentioned in this context.

The solution polymerization may be carried out in water as the solvent. The solution polymerization may occur continuously or discontinuously. A broad range of possible variations with respect to reaction conditions such as temperatures, type, and amount of the initiators as well as the reaction solution can be found in the state of the art. Typical processes are described in the following patent documents: U.S. Pat. No. 4,286,082, DE 27 06 135, U.S. Pat. No. 4,076,663, DE 35 03 458, DE 40 20 780, DE 42 44 548, DE 43 23 001, DE 43 33 056, and DE 44 18 818.

The polymerization may be started by means of an initiator, as is commonly the case. As initiator for the initiation of the polymerization, all initiators that form radicals under the polymerization conditions may be used, which are commonly used in the production of superabsorbers. An initiation of the polymerization through the action of electron beams on the polymerizable, aqueous mixture may be possible. The polymerization may also be started in the absence of initiators of the above-mentioned type by the action of energetic radiation in the presence of photo-initiators. Polymerization initiators may be dissolved or dispersed in a solution of monomers according to the invention. As initiators, all compounds known to the skilled person which decompose into radicals may be considered. In particular, those initiators which have already been mentioned in WO 2004/037903 A2 as possible initiators fall into this group. A redox system consisting of hydrogen peroxide, sodium peroxodisulfate, and ascorbic acid may be used.

Inverse suspension and emulsion polymerization may also be applied to the production of the polymer structures. According to these processes, an aqueous, partially neutralized solution of the monomers ($\alpha1$) and ($\alpha2$), optionally comprising water-soluble polymers and additives, may be dispersed with the aid of protective colloids and/or emulsifying agents in a hydrophobic organic solvent and the polymerization started by radical initiators. The crosslinkers may be either dissolved in the monomer solution and are dosed together with this solution, or are added separately and optionally during the polymerization. Optionally, the addition of a water-soluble polymer ($\alpha4$) as graft basis occurs by means of the monomer solution or by direct presentation into the oil phase. The water may then be removed azeotropically and the polymer filtered off.

Furthermore, the crosslinking may occur by polymerization in of the poly-functional crosslinker dissolved in the monomer solution and/or by reaction of suitable crosslinkers with functional groups of the polymers during the polymerization step. The processes are described, for example, in the publications U.S. Pat. No. 4,340,706, DE 37 13 601, DE 28 40 010, and WO 96/05234 A1.

The hydrogels obtained by solution polymerization or by inverse suspension and emulsion polymerization in process step a) may be dried in process step c).

In particular in the case of solution polymerization, the hydrogels may first be comminuted before the drying in an additional process step b). This commination occurs by means of comminuting devices known to the skilled person, such as, for example, a meat grinder ("Fleischwolf").

The drying of the hydrogel preferably may occur in suitable dryers or ovens. As examples are mentioned rotary ovens, fluidized bed dryers, plate dryers, paddle dryers, or infrared dryers. It is further preferred according to the invention that the drying of the hydrogel in process step c) occurs to a water content of from about 0.5 to about 25 wt %, or from about 1 to about 10 wt %, whereby the drying temperatures are generally from about 100 to about 200° C.

The dried water-absorbing polymer structures obtained in process step c) may if they were obtained by solution polymerization, be comminuted in a further process step d) and sieved to the above-mentioned desired particle size. The comminuting of the dried, water-absorbing polymer structures may occur in a suitable mechanical commination device, such as, for example, a ball mill.

Following the drying of the hydrogels and the optionally carried out further confectioning of the dried water-absorbing polymer structures, these may be modified in the surface region in a further process step e) (in addition to the modification with the combination of the metal salt and the oxide of a metal which is described more closely in the following).

Surface post-crosslinking is mentioned here, in which the dried polymer structure or the not yet dried, however, already comminuted hydrogel may be brought into contact with an organic, chemical surface post-crosslinker. If the post-crosslinker is not liquid under the post-crosslinking conditions, then the post-crosslinker may be brought into contact with the polymer particles, or respectively the hydrogel in the form of a fluid $F_2$ comprising the post-crosslinker as well as a solvent. Solvents may include water or organic solvents miscible with water such as, for example, methanol, ethanol, 1-propanol, 2-propanol, or 1-butanol, or mixtures of at least two of these solvents are used. The post-crosslinker may be comprised in the fluid $F_2$ in an amount of from about 5 to about 75 wt %, or from about 10 to about 50 wt %, or from about 15 to about 40 wt %, based upon the total weight of the fluid $F_2$.

The bringing into contact of the polymer structure or respectively of the comminuted hydrogel with the fluid $F_2$ comprising the post-crosslinker preferably may occur in the process according to the invention by good combining of the fluid $F_2$ with the polymer structure.

Suitable mixing aggregates for applying the fluid $F_2$ include Patterson-Kelley mixer, Drais turbulence mixer, Lodige mixer, Ruberg mixer, screw mixer, plate mixer, and fluidized bed mixer, as well as continuously operating vertical mixers, in which the polymer structure is mixed at high frequency by means of rotating knives (Schugi mixer).

In the process according to the invention, during the post-crosslinking, the polymer structure may be brought into contact with at most about 20 wt %, or at most about 15 wt %, or at most about 10 wt %, or at most about 5 wt % of solvent, respectively based upon the weight of the polymer structure.

For polymer structures in the form of ball-shaped particles, it may be that the bringing into contact may occur in such a way that only the outer region, not, however, the inner region of the particulate polymer structures are brought into contact with the fluid $F_2$ and thus with the post-crosslinker.

As post-crosslinkers that may be used in the process according to the invention may include compounds that comprise at least two functional groups which can react with functional groups of a polymer structure in a condensation reaction (=condensation crosslinker), in an addition reaction or in a ring-opening reaction. Post-crosslinkers include those that are mentioned in WO 2004/037903 A2 as crosslinkers of crosslinker class II. Such compounds include condensation crosslinkers such as, for example, diethylene glycol, triethylene glycol, polyethylene glycol, glycerine, polyglycerine, propylene glycol, diethanolamine, triethanolamine, polyoxypropylene, oxyethylene-oxypropylene block co-polymers or oxypropylene-block co-polymers, sorbitan fatty esters, polyoxyethylene sorbitan fatty acid esters, trimethylopropane, pentaerythritol, polycinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, as well as 1,3-dioxolan-2-one.

After the polymer structures or the hydrogels respectively have been brought into contact with the post-crosslinker, or with the fluid comprising the post-crosslinker respectively, they may be heated to a temperature of from about 50 to about 300° C., or from about 75 to about 275° C., or from about 150 to about 250° C., so that, preferably whereby, the outer region of the polymer structures is more strongly crosslinked compared to the inner region (=post-crosslinking). The time duration of the heat treatment is limited by the risk that the desired property profile of the polymer structures may be destroyed as a result of the action of heating.

The above-described surface modification by means of post-crosslinking may also occur at the same time as the modification of the water-absorbing polymer structures with the combination of a metal salt and an oxide of a metal. In this case, the post-crosslinker may be added to the fluid $F_1$ or to bring the fluid $F_1$ and the fluid $F_2$ into contact with the water-absorbing polymer structure at the same time.

In an embodiment of the process according to the invention, the bringing into contact of the untreated water-absorbing polymer structures with the combination of the metal salt and the oxide of a metal may occur after the water-absorbing polymer structures have been post-crosslinked with a post-crosslinker mentioned in WO 2004/037903 A2 as crosslinker of crosslinker class II.

In another embodiment of the process according to the invention, the bringing into contact of the untreated water-absorbing polymer structure with the combination of the metal salt and the oxide of a metal may occur at the same time as the bringing into contact of the water-absorbing polymer structure with a post-crosslinker as mentioned in WO 2004/037903 A2 as crosslinker of crosslinker class II, whereby in this case one may add the crosslinker of crosslinker class II to the fluid $F_1$. In this case, one may heat the untreated water-absorbing polymer structure brought into contact with the fluid $F_1$ comprising the metal salt, the oxide of the metal, and the crosslinker of crosslinker class II to a temperature of from about 50 to about 300° C., or from about 75 to about 275° C., or from about 150 to about 250° C.

In a further embodiment of the process according to the invention, the bringing into contact of the untreated water-absorbing polymer structure with the combination of the metal salt and the oxide of a metal may occur before the water-absorbing polymer structure has been brought into contact with a post-crosslinker mentioned as crosslinker of crosslinker class II in WO 2004/037903 A2.

According to a particular embodiment of the process according to the invention for treatment of the surface of water-absorbing polymer structures, in a process step ii) the surface of the untreated water-absorbing polymer structure may be brought into contact with the metal salt and the oxide of a metal, whereby both the metal salt and the oxide of a metal may be present in the form of powder.

In this particular embodiment of the process according to the invention for the treatment of the surface of water-absorbing polymer structures, the process may comprise the following process steps:
i) providing the untreated, or an already surface post-crosslinked water-absorbing polymer structure;
ii) bringing into contact of the untreated, or the already surface post-crosslinked water-absorbing polymer structure with a fine particulate component comprising a combination of a metal salt and an oxide of a metal, at a temperature of from about 30 to about 300° C., or from about 100 to about 300° C., or from about 125 to about 250° C., or from about 150 to about 200° C.

In this context, at least about 50 wt. %, or at least about 75 wt %, or at least about 95 wt %, or at least about 99 wt % of the metal salt that may be present in powder form may have an average particle diameter (weight average) of from about 10 to about 1000 µm, or from about 50 µm to about 800 µm, or from about 100 to about 600 µm, or from about 200 to about 400 µm, respectively determined by means of processes known to the skilled person for determination of particle size, for example by sieve analysis or by means of a Coulter counter. At least about 50 wt %, or at least about 75 wt %, or at least about 90 wt % of the metal oxide may have a particle size determined by sieve analysis (for particle sizes larger than about 10 µm) or laser diffractometry (for particle sizes smaller than about 10 µm) of from about 10 to about 1,000,000 nm, or from about 12 to about 500,000 nm, or from about 15 to about 5,000 nm. The oxide of the metal may have a weight average of the particle size of from about 15 to about 5,000 nm, or from about 20 to about 3,000 nm, or from about 100 to about 2,000 nm.

Furthermore, if the fine particulate component, in addition to the powdery metal salt and the powdery oxide of a metal, may additionally comprise a binder, whereby this binder may be present in particulate form and may be based to at least about 50 wt %, or to at least about 75 wt %, or to at least about 95 wt %, or to at least about 99 wt % on particles with an average particle size (weight average) of from about 10 to about 1,000 µm, or from about 50 µm to about 800 µm, or from about 100 to about 600 µm, or from about 200 to about 400 µm, respectively determined by processes known to the skilled person for particle size determination, for example by sieve analysis or by means of a Coulter counter. The binder may comprise as a binder principal component, an organic compound, whereby the organic compound may be a solid at about 20° C.

The organic compound may be a linear polymer from polyurethenes, polyesters, polyamides, polyesteramides, polyolefins, polyvinylesters, polyethers, polystyrenes, polyimides, in particular polyetherimides, polyimines, sulphur polymers, in particular polysulphones, polyacetals, in particular polyoxymethylenes, fluorine-plastics, in particular polyvinylidenefluoride, styrene-olefin-copolymers, polyacrylates, ethylene-vinylacetate copolymers, or mixtures of two or more of the polymers mentioned. Particularly suitable linear polyethers may comprise polyalkylene glycols, in particular polyethylene glycols, polypropylene glycols, poly (ethylene/propylene)glycols with statistical or block-like arrangement of the ethylene or propylene monomers or mixtures of at least two of these polyalkylene glycols.

Further suitable linear polymers may be those polymers that are mentioned in DE-A-10334286 as "thermoplastic adhesives" ("thermoplastische Klebstoffe").

If a binder may be used in addition to the metal salt and the oxide of a metal, the bringing into contact of the surface of the untreated water-absorbing polymer structure with the fine particulate component may occur at a temperature of from about 30 to about 200° C., or from about 50 to about 160° C., or from about 70 to about 140° C. At these temperatures, it may lead to an immobilization of the fine particulates on the surface of the untreated water-absorbing polymer structure.

The amount of the binding agent, if used, may lie within a range from 0.0001 to about 5 wt %, or from about 0.001 to about 2 wt %, respectively based on the weight of the water-absorbing polymer structure. The weight ratio between fine particulate component and binder may lie within a range of fine particulate component:binder from about 20:1 to about 1:20, or from about 10:1 to about 1:10, or from about 10:1 to 2:1.

In the above-described, particular embodiment of the process according to the invention, in which a powdery metal salt and a powdery oxide of a metal may be used for treatment of the surface of water-absorbing polymer structures, the process may also comprise, in addition to the provision of the untreated water-absorbing polymer structure, in process step i) the provision of a fine particulate component comprising the combination of powdery metal salt and powdery metal oxide as well as powdery binder. With respect to the method of the bringing into contact of the fine particulate component with the untreated water-absorbing polymer structure, different processes are conceivable:

According to variant $V_A$ in process step ii), firstly a mixture of fine particulate component and water-absorbing polymer structures may be prepared, and this may be then heated at the above-mentioned temperatures to cause an immobilization of the fine particulates, whereby the water-absorbing polymer structure may already be surface post-crosslinked, or whereby the water-absorbing polymer structure may have already been brought into contact with the post-crosslinker, but may not yet have been heated to a temperature necessary for a surface post-crosslinking.

According to variant $V_B$, firstly, before process step ii), the water-absorbing polymer structures may be heated to the above-described temperature, and then in process step ii), these pre-heated water-absorbing polymer structures may be combined with the fine particulate component which has not been pre-heated.

According to variant $V_C$, firstly, before process step ii), the water-absorbing polymer structures and the fine particulate components may be respectively separately heated to the above-described temperature, and then in process step ii), the pre-heated water-absorbing polymer structures may be combined with the likewise pre-heated fine particulate component. According to a particular embodiment of this variant $V_C$, the fine particulate component may be cooled after the heating, and before the combining with the pre-warmed water-absorbing polymer structure, to a temperature of from about 10 to about 100° C., or from about 15 to about 75° C., or from about 20 to about 60° C., afterwards optionally to comminute, for example using a pestle and mortar, and then to combine the cooled and optionally comminuted fine particulate component with the pre-warmed water-absorbing polymer structures.

According to variant $V_D$, before process step ii), the fine particulate components may be heated to the above-described temperature, and then in process step ii), the pre-heated fine particulate component may be combined with the non-pre-heated, water-absorbing polymer structures. According to a particular embodiment of this variant $V_D$, the fine particulate component may be cooled after the heating and before the combining with the pre-warmed water-absorbing polymer structure, preferably to a temperature of from about 10 to about 100° C., or from about 15 to about 75° C., or from about 20 to about 60° C., afterwards optionally to comminute, for example using a pestle and mortar, and then to combine the cooled and optionally comminuted fine particulate component with the not pre-warmed water-absorbing polymer structures.

Furthermore, it may be advantageous in respect of the above described particular embodiment of the process according to the invention, in which a powdery metal salt and a powdery oxide of a metal may be used for treatment of the surface of water-absorbing polymer structures, if a further process step iii), in which the mixture of water-absorbing polymer structure and fine particulate components may be mixed for a time of from about 10 minutes to about 5 hours, or from about 30 minutes to about 3 hours, follows process step ii), in order to enable as homogeneous distribution as possible of the fine particulates or respectively the fine particulate agglomerates and the absorbing polymer structure, whereby, to this end, mixing devices known to the skilled person can be used. In this further process step, the mixture of untreated, water-absorbing polymer structure and fine particulate component may be introduced into the mixer with the temperature which it has after the immobilization in process step ii), whereby the mixture can than be cooled during the mixing preferably constantly to a lower temperature, or to room temperature.

A further contribution to the solution of the above-mentioned object is provided by the surface-treated water-absorbing polymer structures obtainable by the process according to the invention.

The above-described water-absorbing polymer structures according to the present invention may have the same properties as the surface-treated water-absorbing polymer structures obtainable by the process according to the invention. Each value that has been given in the context of the process according to the invention and the polymer structures according to the invention as lower limits of features according to the invention without upper limits, have upper limits of about 20 times, or about 10 times, or about 5 times the most preferred value of the lower limit.

A further contribution to solving the above-described objects is delivered by a composite comprising the surface-treated water-absorbing polymer structures according to the invention or respectively the surface-treated water-absorbing polymer structures obtainable by a process according to the invention and a substrate. The polymer structures according to the invention and the substrate may be firmly joined together with each other. Substrates may include sheets made from polymers, such as, for example, polyethylene, polypropylene or polyamide, metals, non-wovens, fluff, tissues, woven materials, natural or synthetic fibers, or other foams. The composite may comprise at least one region, which comprises the water-absorbing polymer structure according to the invention in an amount of from about 15 to about 100 wt %, or from about 30 to about 100 wt %, or from about 50 to 99.99 wt %, or from about 60 to about 99.99 wt %, or from about 70 to about 99 wt %, respectively based on the total weight of the composite, whereby this region preferably has a size of at least about 0.01 cm³, or at least about 0.1 cm³, or at least about 0.5 cm³.

The composite according to the invention such as a sheet-like composite, is described in WO-A-02/056812 as "absorbent material". The disclosure of WO-A-02/056812, in particular with respect to the exact construction of the composite, the mass per unit area of its components and of its thickness is hereby introduced as reference and represents a part of the disclosure of the present invention.

A further contribution to the solution of the above-mentioned objects is provided by a process for production of a composite, whereby the water-absorbing polymer structures according to the invention or respectively the surface-treated water-absorbing polymer structures obtainable by the process according to the invention and a substrate and optionally an additive may be brought into contact with each other. The substrates that were mentioned above in the context of the composite, according to the invention, may be used.

According to a particular embodiment of the process according to the invention for producing a composite, this process comprises the following process steps:
I) provision of a substrate;
II) provision of an untreated, preferably, however, already surface post-crosslinked water-absorbing polymer structure;
III) provision of a fine particulate component;
IV) bringing into contact of the substrate with the water-absorbing polymer structure;
V) bringing into contact of the water-absorbing polymer structure with the fine particulate component; and
VI) immobilization of at least a part of the fine particulates on the surface of the water-absorbing polymer structures.

Each fine particulate component which has already been described above may be used in connection with the particular embodiment of the process according to the invention for treatment of the surface of water-absorbing polymer structure. An example is a mixture of powdery metal salt, powdery oxide of a metal, and powdery binder.

According to a variant of this particular embodiment of the inventive process for production of a composite, first the substrate and the water-absorbing polymer structure may be brought into contact with each other, by first providing the substrate, and then sprinkling the polymer structure either uniformly or on defined areas of the substrate surface. The water-absorbing polymer structures situated on the substrate surface may then be brought into contact with the fine particulate component, for example by sprinkling the fine particulate component on the polymer structure situated on the substrate surface. The immobilization of the fine particulate components on the surface of the polymer structure may then occur, whereby this immobilization may occur by the heating described above in connection with the inventive process for treatment of the surface of water-absorbing polymer structures. In this variant of the particular embodiment of the inventive process for production of a composite, process step V) therefore occurs after process step IV).

According to another variant of this particular embodiment of the inventive process for production of a composite, first the substrate is provided. Then the water-absorbing polymer structure may be brought into contact with the substrate, by first providing the substrate and then sprinkling the surface post-crosslinked polymer structure either uniformly or on defined areas of the substrate surface. Before the polymer structure is brought into contact with the substrate surface, the water-absorbing polymer structures are brought into contact with the fine particulate component, for example by combining the fine particulate component with the polymer structure before it is sprinkled onto the substrate surface. After the polymer structures have been brought into contact with the substrate, the immobilization of the fine particulate component on the surface of the polymer structure occurs. In this variant of the particular embodiment of the inventive process for production of a composite, process step V) therefore occurs before process step IV).

A contribution to the solution of the above-mentioned objects is also provided by a composite obtainable by the above-described process, whereby this composite may have the same properties as the above described composite according to the invention.

A further contribution to the solution of the above-mentioned objects may be provided by chemical products comprising the water-absorbing polymer structures according to the invention or a composite according to the invention. The chemical products may include foams, formed bodies, fibers, sheets, films, cables, sealing materials, liquid-absorbing hygiene articles, in particular diapers and sanitary napkins, carriers for plant- or fungus-growth-regulating agents or plant protection active substances, additives for construction materials, packaging materials, or soil additives.

The use of the water-absorbing polymer structures according to the invention or of the composite according to the invention in chemical products as listed above, in particular in hygiene articles such as diapers or sanitary napkins, as well as the use of the superabsorber particles as carrier for plant- or fungus-growth-regulating agents or plant protection active substances also provide a contribution to the solution of the above-mentioned objects. In the use as carrier for plant- or fungus-growth-regulating agents or plant protection active substances, it is preferred that the plant- or fungus-growth-regulating agent or plant protection active substances can be released over a time period controlled by the carrier.

A further contribution to the solution of the above-mentioned objects may be provided by the use of a combination of a metal salt and an oxide of a metal for treatment of the surface of water-absorbing polymer structures, preferably for improvement of the retention capacity of water-absorbing polymer structures, whereby as metal salt and as oxide of a metal, those compounds are preferred which have already been mentioned above in connection with the water-absorbing polymer structures according to the invention as preferred components ($\alpha 4$) and ($\alpha 5$).

The invention is now illustrated by means of non-limiting examples.

EXAMPLES

Preparation of SAP Particles

A monomer solution consisting of 600 g acrylic acid, which was neutralized to 70 mol % with sodium hydroxide solution (466.22 g 50% NaOH) 881.52 g water, 0.573 g polyethyleneglycol-300-diacrylate, 1.603 g monoallylpolyethyleneglycol-450-monoacrylic acid ester and 17.2 g polyethylene glycol-750-monomethacrylic acid ester methyl ether was flushed with nitrogen to remove dissolved oxygen and cooled to the start temperature of 4° C. After the start temperature was reached, the initiator solution (0.6 g sodium peroxydisulfate in 10 g $H_2O$, 0.014 g 35% hydrogen peroxide solution in 10 g $H_2O$ and 0.03 g ascorbic acid in 10 g $H_2O$) was added. After the end temperature of about 100° C. was reached, the resulting gel was comminuted with a meat grinder ("Fleischwolf") and dried at 150° C. for 2 hours in the drying cupboard. The dried polymer was coarsely broken up, milled using a cutting mill ("Schneidmühle") SM10 with a 2 mm sieve and sieved to a powder with a particle size of 150 to 850 µm (=powder A).

Comparative Example

Usual Post-Crosslinking 100 g of powder A were combined with a solution consisting of 1.0 g ethylene carbonate, 0.2 g $Al_2(SO_4)_3 \times 14H_2O$, and 2.5 g deionized water, whereby the solution was applied to the polymer powder in a mixer by means of a syringe with a 0.45 mm cannula. The powder A coated with the aqueous solution was then heated in a circulating air oven at 170° C. for 45 minutes. A powder B was obtained.

Example 1

A solution of 150 g deionized water, 12 g $Al_2(SO_4)_3 \times 14H_2O$, 12 g Nanox®200 (zinc oxide powder of the company Elementis Specialities, USA, with a BET-surface of 17 $m^2/g$ and an average particle size of 60 nm) and 60 g ethylene carbonate was combined using an Ultra Turax to form a dispersion. 3.9 g of this suspension were added to 100 g of the polymer powder A in a mixer, by means of a syringe with a 0.9 mm cannula. The powder A coated with the suspension was then heated in a circulating air cupboard at 170° C. for 45 minutes. A powder C was obtained. The R/LA ratio was 2.01 g/g %.

Example 2

A solution of 150 g deionized water, 18 g $Al_2(SO_4)_3 \times 14H_2O$, 18 g Nanox® 200 (zinc oxide powder of the company Elementis Specialities, USA, with a BET-surface area of 17 $m^2/g$ and an average particle size of 60 nm) and 60 g ethylene carbonate was combined using an Ultra Turax to form a dispersion. 4.1 g of this suspension were applied to 100 g of the polymer powder A in a mixer by means of a syringe with a 0.9 mm cannular. The powder A coated with the suspension was then heated in a circulating air cupboard at 170° C. for 45 minutes. A powder D was obtained. The R/LA ratio was 2.05 g/g %.

Example 3

A solution of 150 g deionized water, 24 g $Al_2(SO_4)_3 \times 14H_2O$, 30 g Nanox® 200 (zinc oxide powder of the company Elementis Specialties, USA, with a BET-surface area of 17 $m^2/g$ and an average particle size of 60 nm) and 60 g ethylene carbonate was combined using an Ultra Turax to form a dispersion. 4.4 g of this suspension were applied to 100 g of the polymer powder A in a mixer by means of a syringe with a 0.9 mm cannular. The powder A coated with the suspension was then heated in a circulating air cupboard at 170° C. for 45 minutes. A powder E was obtained. The R/L ratio was 2.00 g/g %. The polymer powders have the following absorption properties:

| Powder | Coating with | | | CRC value [g/g] |
|---|---|---|---|---|
| | Ethylene carbonate [wt. %] | Aluminum sulphate [wt. %] | Nanox ® 200 [wt. %] | |
| A | 0 | 0 | 0 | 39.9 |
| B | 1.0 | 0.2 | 0 | 32.7 |
| C | 1.0 | 0.2 | 0.2 | 34.2 |
| D | 1.0 | 0.3 | 0.3 | 34.8 |
| E | 1.0 | 0.4 | 0.5 | 34.0 |

As can be seen from the above absorption values, by means of the surface treatment according to the invention of the polymer structures with the metal salt (aluminum sulphate) and the oxide of a metal (Nanox® 200), the decrease in the CRC value observed when surface post-crosslinking can be noticeably reduced.

Example 4

The polymers obtained in the production example were post-crosslinked as described in the comparative example, but without addition of $Al_2(SO_4)_3 \times 14H_2O$ in the post-crosslinker solution. 100 g of the thus obtained polymers were pre-heated in the drying oven to 130° C.

A mixture of 24 g $Al_2(SO_4)_3 \times 14H_2O$, which had been milled in a centrifugal mill and sieved to a particle size within a range from 300 to 400 µm, 30 g Nanox® 200 (zinc oxide powder from the company Elementis Specialities, USA, with a BET surface area of 17 $m^2/g$ and an average particle size of 60 nm) and 3.6 g polyethylene glycol 10,000 (polyethylene glycol with a molecular weight of 10,000 g/mol), which had likewise been milled in a centrifugal mill and sieved to a particle size of less than 300 µm, was prepared. 1.15 g of this mixture were combined in a Kirups mixer by stirring with the pre-heated water-absorbing polymer structure.

The invention claimed is:

1. A water-absorbing polymer structure, which is based at least to 50 wt. % on carboxylate groups containing monomers wherein the water-absorbing polymer structure has been dried and comminuted into dried water-absorbing polymer structure particles wherein at least 50 wt % of the dried water-absorbing polymer structure particles have a particle size of from 300 µm to 600 µm wherein the dried water-absorbing polymer structure particles have an inner region and an outer region surrounding the inner region wherein the surface of the water-absorbing polymer structure particles has been brought into contact with a combination of an organic post-crosslinker, a metal salt of a bivalent or trivalent metal cation and zinc oxide, wherein at least 50 wt. % of the zinc oxide have a particle size in a range of 10 to 5,000 nm and wherein the metal salt is a water-soluble metal salt wherein the metal salt has a water-solubility at a temperature of 25° C. of at least 100 g in 1 liter of distilled water; and the contacted water-absorbing polymer structure particles have been heated to a temperature of from 150° C. to 250° C. whereby the outer region of the water-absorbing polymer structure particles is more strongly crosslinked than the inner region.

2. The water-absorbing polymer structure according to claim 1 wherein the polymer structure has an R/L-ratio of at least 2.00 g/g %.

3. The water-absorbing polymer structure according to claim 1, wherein the metal salt is a sulfate.

4. A water-absorbing polymer structure according to claim 1 wherein the organic post-crosslinker comprises ethylene carbonate.

5. A process for treatment of the surface of water-absorbing polymer structures, comprising the process steps:
   i) providing an untreated water-absorbing polymer structure which is based to at least 50 wt. % on carboxylate groups containing monomers;
   ii) drying the untreated water-absorbing polymer structure to form dried water-absorbent polymer structures;
   iii) comminuting the dried water-absorbent polymer structures into dried water-absorbing polymer structure particles wherein at least 50 wt % of the dried water-absorbing polymer structure particles have a particle size of from 300 µm to 600 µm wherein the dried water-absorbing polymer structure particles have an inner region and an outer region surrounding the inner region
   iv) bringing into contact the surface of the dried water-absorbing polymer structure particles with a combination of an organic post-crosslinker, a metal salt of a bivalent or trivalent metal cation and zinc oxide at a temperature from 150 to 250° C., wherein at least 50 wt. % of the zinc oxide has a particle size from 10 to 5,000 nm, and wherein the metal salt is a water soluble metal salt having a water-solubility at a temperature of 25° C. of at least 100 g in 1 liter of distilled water;
whereby the outer region of the dried water-absorbing polymer structure particles is more strongly crosslinked than the inner region.

6. The process according to claim 5 wherein the metal salt and the zinc oxide in the form of a fluid $F_1$ comprising a solvent, the metal salt, and the zinc oxide are brought into contact with the water-absorbing polymer structure.

7. The process according to claim 6, wherein the fluid $F_1$ additionally comprises an organic post-crosslinker which is capable of reacting in a condensation reaction with functional groups of the water-absorbing polymer structure.

8. The process according to claim 5 wherein the metal salt in an amount from 0.001 to 5 wt. % and the zinc oxide in an amount from 0.001 to 5 wt. %, respectively based on the weight of the untreated water-absorbing polymer structure, are brought into contact with the untreated water-absorbing polymer structure.

9. The process according to claim 5 wherein the metal salt is a salt of aluminum.

10. A composite comprising a water-absorbing polymer structure according to claim 1 and a substrate.

* * * * *

UNITED STATES PATENT AND TRADEMARK OFFICE
CERTIFICATE OF CORRECTION

| | |
|---|---|
| PATENT NO. | : 8,247,499 B2 |
| APPLICATION NO. | : 11/912219 |
| DATED | : August 21, 2012 |
| INVENTOR(S) | : Mirko Walden, Franck Furno and Harald Schmidt |

It is certified that error appears in the above-identified patent and that said Letters Patent is hereby corrected as shown below:

Column 3,
Please insert the following heading immediately after Line 20:

-- DESCRIPTION --.

Column 10,
Line 17, "polycinyl alcohol," should read -- polyvinyl alcohol --.

Signed and Sealed this
Sixteenth Day of October, 2012

David J. Kappos
*Director of the United States Patent and Trademark Office*